United States Patent
Lubock et al.

(10) Patent No.: US 7,413,539 B2
(45) Date of Patent: Aug. 19, 2008

(54) TREATMENT OF A BODY CAVITY

(75) Inventors: Paul Lubock, Laguna Niguel, CA (US); Michael L. Jones, San Clemente, CA (US)

(73) Assignee: SenoRx, Inc.

( * ) Notice: Subject to any disclaimer, the term of this patent is extended or adjusted under 35 U.S.C. 154(b) by 0 days.

(21) Appl. No.: 11/283,236

(22) Filed: Nov. 18, 2005

(65) Prior Publication Data

US 2007/0129592 A1 Jun. 7, 2007

(51) Int. Cl.
*A61N 5/00* (2006.01)
(52) U.S. Cl. .......................................................... 600/3
(58) Field of Classification Search .................... 600/30,
600/407, 424, 427, 1–9; 604/508–509, 19–21,
604/27–28, 48, 73, 93.01, 95.03, 96.01, 101.01–101.05,
604/102.01–102.03, 103.05–103.07, 103.1,
604/104, 158–159, 164.01, 164.08, 171,
604/263–264, 500, 506–511, 514–517; 601/1,
601/15, 111, 112, 118, 119; 606/1, 32–34,
606/41; 607/1–2, 100, 101, 122, 154–156
See application file for complete search history.

(56) References Cited

U.S. PATENT DOCUMENTS

| | | | |
|---|---|---|---|
| 4,690,677 A * | 9/1987 | Erb | 604/329 |
| 5,106,360 A | 4/1992 | Ishiwara et al. | |
| 5,167,622 A | 12/1992 | Muto | |
| 5,342,305 A | 8/1994 | Shonk | |
| 5,417,687 A | 5/1995 | Nardella et al. | |
| 5,611,767 A | 3/1997 | Williams | |
| 5,621,780 A * | 4/1997 | Smith et al. | 378/65 |
| 5,662,580 A | 9/1997 | Bradshaw et al. | |
| 5,863,285 A | 1/1999 | Coletti | |
| 5,913,813 A | 6/1999 | Williams et al. | |
| 5,931,774 A | 8/1999 | Williams et al. | |
| 6,022,308 A | 2/2000 | Williams | |
| 6,036,631 A * | 3/2000 | McGrath et al. | 600/3 |

(Continued)

FOREIGN PATENT DOCUMENTS

EP 0 536 440 4/1993

(Continued)

OTHER PUBLICATIONS

Patent Abstracts of Japan, vol. 2000, No. 22, Mar. 9, 2001 and JP 2001 120561, May 8, 2001.

(Continued)

*Primary Examiner*—John P. Lacyk
(74) *Attorney, Agent, or Firm*—Edward J. Lynch

(57) ABSTRACT

Devices and methods are provided for controlled application of a treatment to tissue adjacent a body cavity, such as after removal of tissue, e.g. cancer. A device embodying features of the invention includes one or more radiation shielding components to control emitted radiation from a radiation source to minimize radiation damage to healthy portions of the body cavity. A device embodying features of the invention can include a sealing member at a location on a shaft of the device proximal to a treatment location therein to seal the passageway leading to the body cavity. Methods for treating a body cavity include methods for delivering a radiation source to a body cavity while minimizing damaging irradiation of healthy tissue.

45 Claims, 7 Drawing Sheets

U.S. PATENT DOCUMENTS

| | | |
|---|---|---|
| 6,083,148 A | 7/2000 | Williams |
| 6,390,967 B1 * | 5/2002 | Forman et al. ............ 600/3 |
| 6,413,204 B1 | 7/2002 | Winkler et al. |
| 6,416,492 B1 * | 7/2002 | Nielson ............ 604/22 |
| 6,458,069 B1 | 10/2002 | Tam et al. |
| 6,482,142 B1 | 11/2002 | Winkler et al. |
| 6,540,655 B1 * | 4/2003 | Chin et al. ............ 600/3 |
| 6,673,006 B2 | 1/2004 | Winkler |
| 6,706,014 B2 * | 3/2004 | Banik et al. ............ 604/103.01 |
| 6,913,600 B2 * | 7/2005 | Valley et al. ............ 604/96.01 |
| 2001/0016725 A1 * | 8/2001 | Valley et al. ............ 604/509 |
| 2001/0049464 A1 | 12/2001 | Ganz |
| 2002/0045893 A1 | 4/2002 | Lane et al. |
| 2002/0095114 A1 | 7/2002 | Palasis |
| 2002/0177804 A1 | 11/2002 | Saab |
| 2004/0054366 A1 * | 3/2004 | Davison et al. ............ 606/39 |
| 2004/0087827 A1 | 5/2004 | Lubock |
| 2004/0116767 A1 | 6/2004 | Lebovic et al. |
| 2004/0215048 A1 | 10/2004 | Lubock |
| 2005/0080313 A1 * | 4/2005 | Stewart et al. ............ 600/3 |
| 2005/0182286 A1 | 8/2005 | Lubock |
| 2005/0240074 A1 | 10/2005 | Lubock |

FOREIGN PATENT DOCUMENTS

| | | |
|---|---|---|
| WO | WO 02/09599 | 2/2002 |
| WO | WO 02/069862 | 9/2002 |

OTHER PUBLICATIONS

Patent Abstracts of Japan, vol. 1998, No. 10, Aug. 31, 1998, and JP 10 137250, May 26, 1998.

* cited by examiner

TREATMENT OF A BODY CAVITY

FIELD OF THE INVENTION

This invention relates generally to the fields of medical treatment devices and methods. In particular, the invention relates to devices and methods for treating tissue surrounding a body cavity, such as a site from which cancerous, pre-cancerous, or other tissue has been removed.

BACKGROUND OF THE INVENTION

In diagnosing and treating certain medical conditions, it is often desirable to perform a biopsy, in which a specimen or sample of tissue is removed for pathological examination, tests and analysis. A biopsy typically results in a biopsy cavity occupying the space formerly occupied by the tissue that was removed. As is known, obtaining a tissue sample by biopsy and the subsequent examination are typically employed in the diagnosis of cancers and other malignant tumors, or to confirm that a suspected lesion or tumor is not malignant. Treatment of cancers identified by biopsy may include subsequent removal of tissue surrounding the biopsy site, leaving an enlarged cavity in the patient's body. Cancerous tissue is often treated by application of radiation, by chemotherapy, or by thermal treatment (e.g., local heating, cryogenic therapy, and other treatments to heat, cool, or freeze tissue).

Cancer treatment may be directed to a natural cavity, or to a cavity in a patient's body from which tissue has been removed, typically following removal of cancerous tissue during a biopsy or surgical procedure. For example, U.S. Pat. No. 6,923,754 to Lubock and U.S. patent application Ser. No. 10/849,410 to Lubock, the disclosures of which are all hereby incorporated by reference in their entireties, describe devices for implantation into a cavity resulting from the removal of cancerous tissue which can be used to deliver cancer treatments to surrounding tissue. One form of radiation treatment used to treat cancer near a body cavity remaining following removal of tissue is "brachytherapy" in which a source of radiation is placed near to the site to be treated.

Lubock above describes implantable devices for treating tissue surrounding a cavity left by surgical removal of cancerous or other tissue that includes an inflatable balloon constructed for placement in the cavity. Such devices may be used to apply one or more of radiation therapy, chemotherapy, and thermal therapy to the tissue surrounding the cavity from which the tissue was removed. The delivery lumen of the device may receive a solid or a liquid radiation source. Radiation treatment is applied to tissue adjacent the balloon of the device by placing radioactive material such as radioactive "seeds" in a delivery lumen. Such treatments may be repeated if desired.

For example, a "MammoSite® Radiation Therapy System" (MammoSite® RTS, Proxima Therapeutics, Inc., Alpharetta, Ga. 30005 USA) includes a balloon catheter with a radiation source that can be placed within a tumor resection cavity in a breast after a lumpectomy. It can deliver a prescribed dose of radiation from inside the tumor resection cavity to the tissue surrounding the original tumor. The radiation source is typically a solid radiation source; however, a liquid radiation source may also be used with a balloon catheter placed within a body cavity (e.g., Iotrex®, Proxima Therapeutics, Inc.). A radiation source such as a minature or microminature x-ray tube may also be used (e.g. U.S. Pat. No. 6,319,188). The x-ray tubes are small, flexible and are believed to be maneuverable enough to reach the desired treatment location within a patient's body. The radiation source is to be removed following each treatment session, or remains in place as long as the balloon remains within the body cavity. Inflatable treatment delivery devices and systems, such as the MammoSite® RTS and similar devices and systems (e.g., GliaSite® RTS (Proxima Therapeutics, Inc.)), are useful to treat cancer in tissue adjacent a body cavity.

However, radiation, chemotherapy, thermal treatment, and other cancer treatments often have deleterious effects on healthy tissue in addition to the desired effects on cancerous tissue. In such treatments, care must be taken to direct the maximum treatment effects to diseased tissue while minimizing its delivery or effects on healthy tissue. For example, radiation treatment may be most effective when only the portion of tissue requiring treatment receives the radiation and where surrounding healthy tissue is unaffected. Tissue cavities typically are not uniform or regular in their sizes and shapes, so that differences in dosages applied to different regions of surrounding tissue, including "hot spots" and regions of relatively low dosage, often result from radiation treatment.

A treatment delivery device for treating tissue adjacent a body cavity has been disclosed in U.S. Pat. No. 6,923,754. This device applies a partial-vacuum or suction to bring tissue towards a radiation source and allows for uniform application of radiation to tissue surrounding a body cavity. An advantage of the present invention is that it allows for the protection of healthy tissue within that body cavity and provides a seal in the passageway leading to the body cavity while treating the desired tissue.

SUMMARY OF THE INVENTION

This invention is generally directed to treating a patient's body cavity, such as by irradiation, and devices and methods for such treatments. The invention is particularly suitable for treating tissue adjacent a patient's body cavity formed by removal of tissue for a biopsy.

More specifically, a device embodying features of the invention includes an elongate shaft with a treatment location at a distal portion of the shaft which is configured to receive or which includes a source for a treatment agent, such as a radiation source. In this embodiment the device has one or more radiation shielding components that control at least in part the radiation emitted from the radiation source.

The radiation shielding component is designed to reduce or minimize damaging irradiation of healthy tissue surrounding the body cavity while treating nearby areas having diseased tissue with radiation emitted from the radiation source. The radiation shielding components include one or more radiation shields disposed about a delivery shaft containing the radiation source. Preferably, the radiation shielding component has a pair of radiation shields one that is deployed proximal and one that is deployed distal to the treatment location to control axial and near axial radiation emissions of the radiation source. The location of the pair of radiation shields is configured to be adjustable to accommodate anatomical structural variations or to adjust treatment parameters. A central radiation shield preferably has or defines at least in part a window to control the dispersal of radiation from a radiation source. The window defined at least in part by the central radiation shield has a length between about 2 millimeters and 5 centimeters. The shielded area of the central radiation shield is arcuate with an angular range from about 20° to about 240°. While the central radiation shield may be utilized by itself, preferably, the central radiation shield is configured to be deployed between the proximal and distal shields such as discussed above.

A device embodying features of another aspect of the invention includes an elongate shaft with a sealing member located on the elongate shaft proximal to the treatment location to seal the intracorporeal passageway through which the device is advanced. The sealing member is expanded or expandable and configured to minimize the loss of vacuum within the body cavity when a vacuum is developed therein. Preferably the sealing member is also configured to seal the passageway when aspirating fluid from the body cavity or delivering fluid, e.g. treatment fluid, to the body cavity.

A device embodying features of the invention preferably has an enlarged or enlargeable cavity filling member at the treatment location which at least in part fills the body cavity. Preferably the cavity filling member is inflatable such as a balloon. The device also includes an inner lumen configured to be in fluid communication with a proximal vacuum source and one or more vacuum ports preferably proximal and or distal to the cavity filling member such as described in U.S. Pat. No. 6,923,754 and co-pending application Ser. No. 10/849,410 filed on May 19, 2004, both of which are assigned to the present assignee. Application of a vacuum within the inner lumen aspirates fluid in the cavity through one or more vacuum ports and the vacuum within the body cavity pulls tissue defining the cavity onto the exterior of the cavity filling member deployed within the cavity.

Methods for treating a body cavity of a patient include methods for delivering a source for a treatment agent such as a radiation source to a body cavity to treat the desired tissue while minimizing damaging irradiation of healthy tissues. More specifically, a method for treating a body cavity includes providing a device having an elongate shaft with a proximal end, a distal end, and a treatment location in a distal portion of the shaft. The method further includes providing a radiation source configured to be deposited in the treatment location and a radiation shielding component configured to control at least in part the emission of radiation emitted from the treatment location. The device is inserted into a body cavity and the radiation source is positioned within the treatment location. The radiation shielding component is positioned to shield portions of the body cavity from radiation emitted from the radiation source.

Enhanced control over the emission of radiation from a radiation source and an improved seal in the passageway leading to the body cavity are provided by the present invention. These and other advantages of the present invention are described in more detail in the following written description and the accompanying exemplary drawings.

DETAILED DESCRIPTION OF THE INVENTION

Figure 1A:
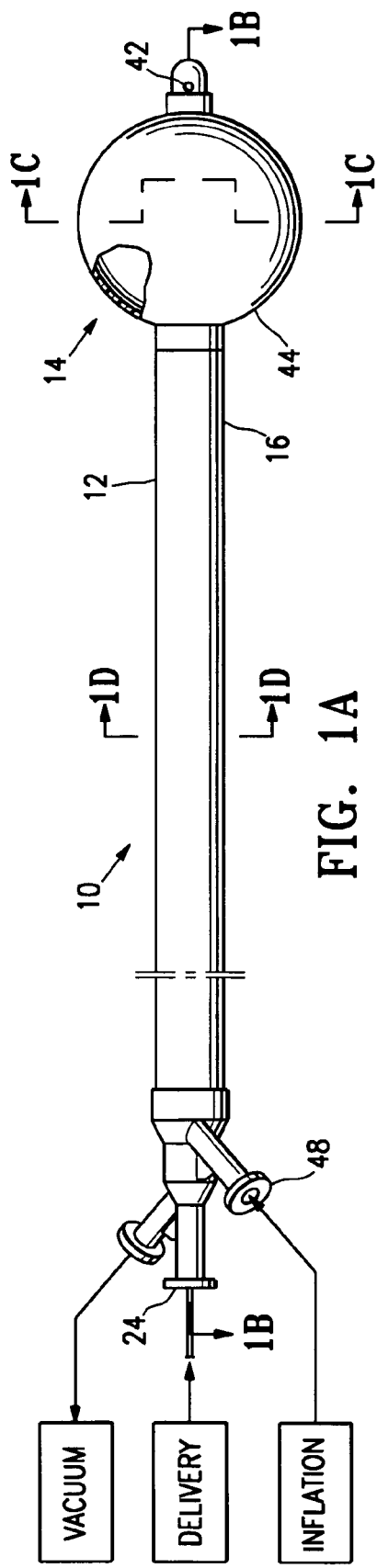
FIG. 1A is a schematic view of a device embodying features of the invention including a cavity filling member.
Figure 1B:
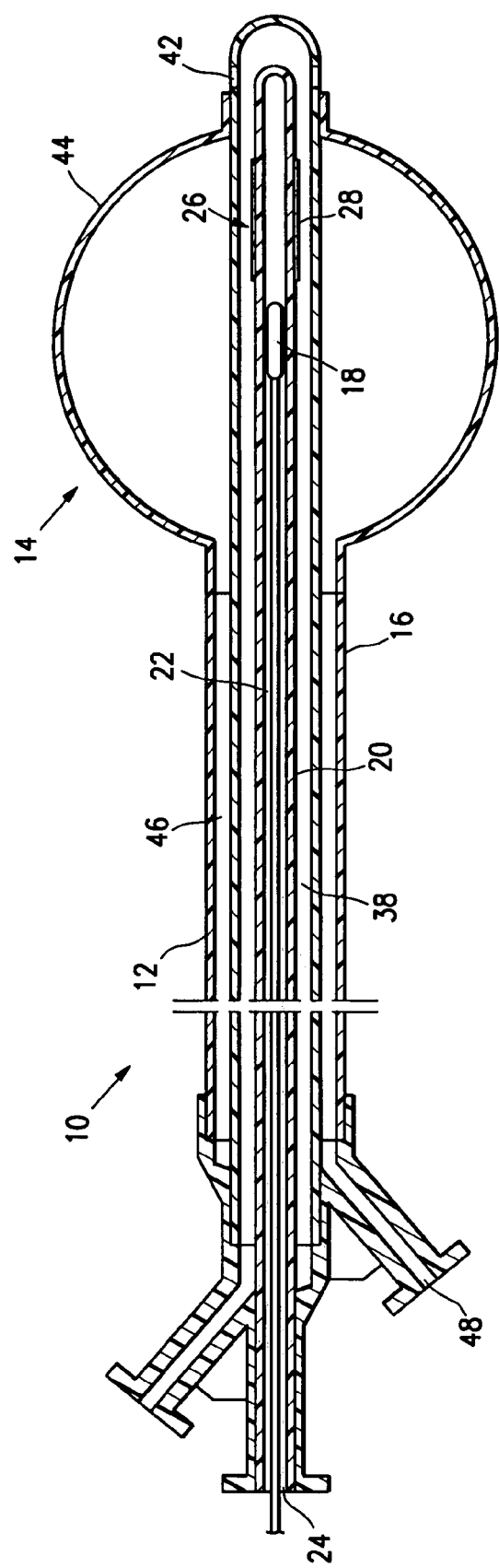
FIG. 1B is a longitudinal cross sectional view of the device along lines 1B-1B in FIG. 1A.
Figure 1D:
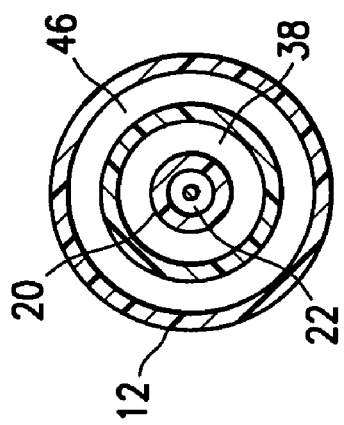
FIG. 1D is a transverse cross sectional view of the device taken along lines 1D-1D.
Figure 1C:
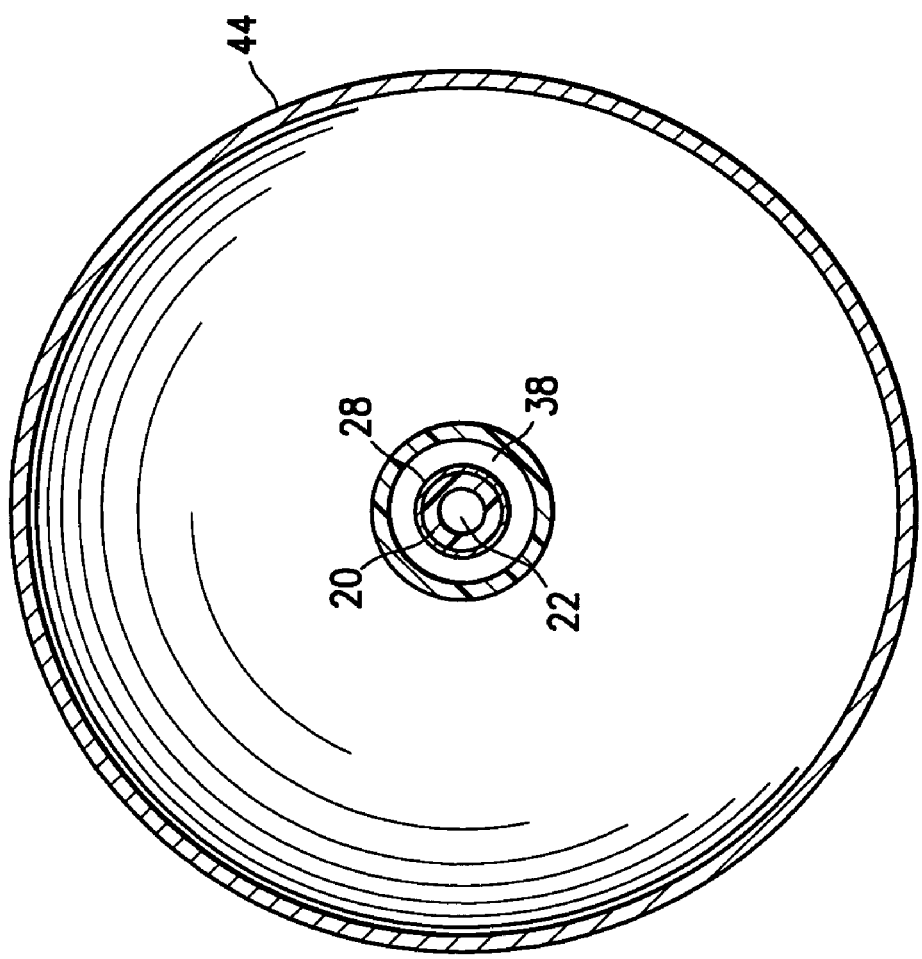
FIG. 1C is a transverse cross sectional view of the device taken along lines 1C-1C in FIG. 1A.

The present invention provides devices and methods for treatment of a patient's body cavity. For example, devices and methods having features of the invention are used to deliver radiation or other treatment into a biopsy site or into a cavity left after removal of cancerous tissue from the patient's body.

As shown in FIGS. 1A-1D a device 10 embodying features of the invention includes an elongated shaft 12 with a treatment location 14 in a distal portion 16 of the elongate shaft 12. The treatment location 14 includes a source for a treatment agent such as a radiation source 18. The elongate shaft 12 contains a delivery shaft 20 having a delivery lumen 22. The delivery shaft 20 also includes a delivery port 24 through which the radiation source 18 is advanced. The device 10 has one or more radiation shielding components 26 disposed about the delivery shaft 20 that control in part the radiation emitted from the radiation source 18. The radiation shielding component 26 is designed to reduce or minimize damaging irradiation of healthy tissue surrounding a body cavity while treating nearby areas having diseased tissue with radiation emitted from the radiation source 18.

Figure 2A:
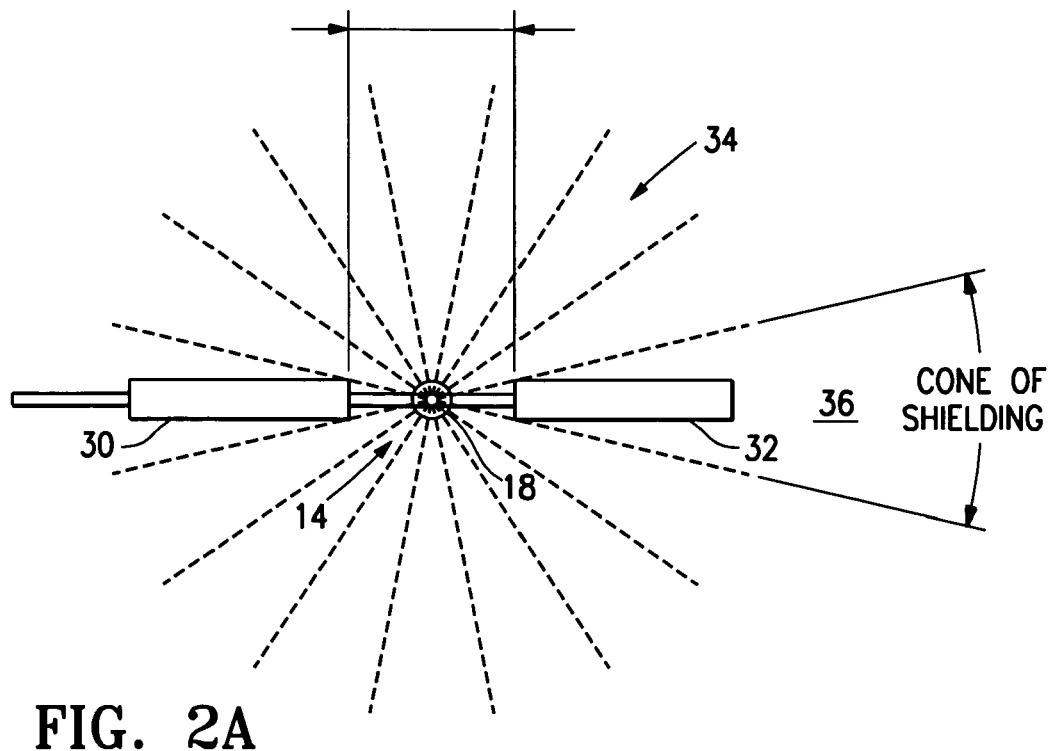
FIGS. 2A and 2B are diagramatic views of a radiation shielding component which includes a proximal radiation shield and a distal radiation shield.
Figure 2B:
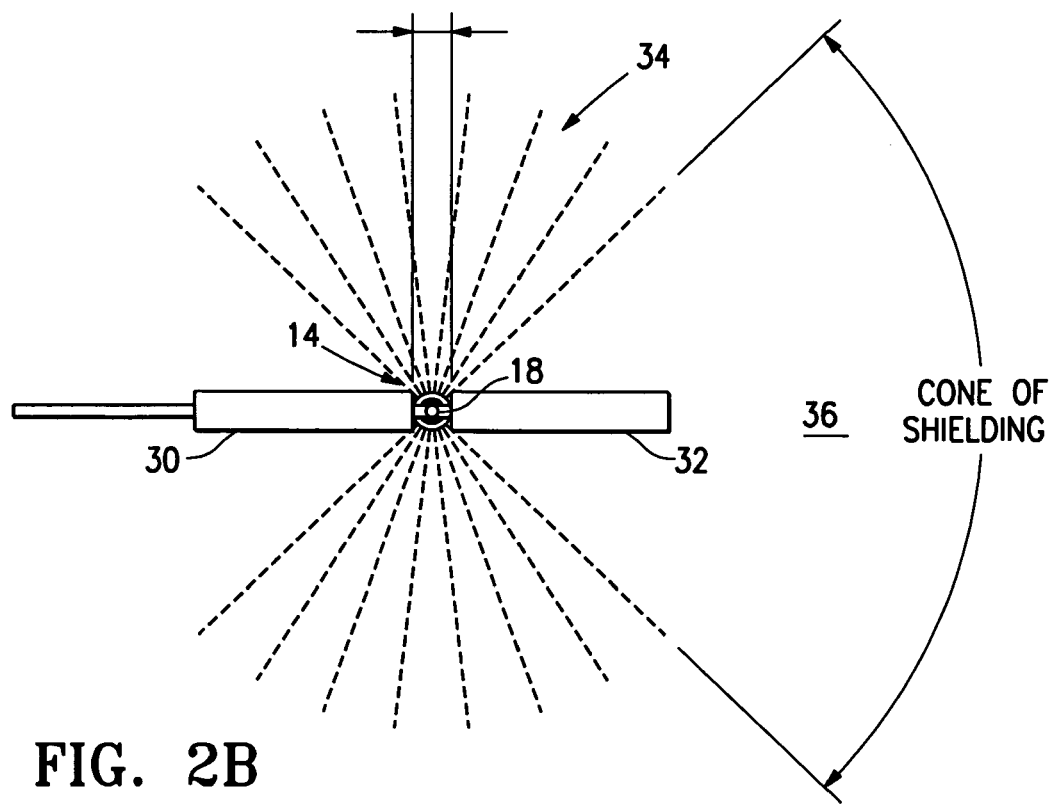

The radiation shielding component 26 includes at least one radiation shield 28 which is configured to be deployed proximal to, distal to, or within the treatment location 14. Preferably, the radiation shielding component 26 has a pair of radiation shields including a proximal radiation shield 30 and a distal radiation shield 32 (FIGS. 2A-2B). The proximal shield 30 is deployed proximal to the treatment location 14 and the distal shield 32 is deployed distal to the treatment location 14. The shields allow for control, at least in part, of the axial and near axial emissions from the proximal and distal end portions of the elongate shaft 12. When the proximal end of distal radiation shield 32 is adjacent the radiation source 18 and the distal end of the proximal radiation shield 30 is adjacent the radiation source 18 the radiation dispersal pattern 34 would be a small cone emanating from the radiation source 18. As the proximal end of the distal radiation shield 32 and the distal end of the proximal radiation shield 30 move further away from the radiation source 18 the radiation dispersal pattern 34 increases to a near spherical shape having an axial cone of shielding 36 expanding from the radiation source 18 along the longitudinal axis in both directions. The pair of radiation shields 30 and 32 are preferably configured to be adjustable to accommodate anatomical structural variations or to adjust treatment parameters.

The radiation shielding component 26 includes one or more radiation shields 28. The radiation shields 28 are formed of a suitably radiopaque metal or polymer containing at least in part a radiation absorbing material and are preferably tubular. The shields are preferably slidably disposed about the delivery lumen 22 of the device 10. Suitable radiation absorbing materials include tantalum, bismuth subcarbonate, barium sulfate, platinum, gold and tungsten.

The radiation source 18 of the device 10 can include a radiation source which is solid or liquid. Suitable liquid radiation sources include, for example, a liquid containing a radioactive iodine isotope (e.g., $I^{125}$ or $I^{131}$), a slurry of a solid isotope, for example, $^{198}AU$ or $^{169}Yb$, or a gel containing a radioactive isotope. Liquid radiation sources are commercially avaliable (e.g., Iotrex.RTM., Proxima Therapeutics, Inc., Alpharetta, Ga.). The radiation source 18 preferably includes brachytherapy seeds or other solid radiation sources used in radiation therapy, for example, a radioactive microsphere available from 3M company of St. Paul, Minn. The radiation source 18 is either preloaded into the device 10 at the time of manufacture or is loaded into the device 10 after placement into a body cavity of a patient. Solid radionuclides suitable for use with a device 10 embodying features of the present invention are currently generally available as brachytherapy radiation sources (e.g., I-Plant™, Med-Tec, Orange City, Iowa.). Radiation may also be delivered by a device such as the x-ray tube of U.S. Pat. No. 6,319,188. The x-ray tubes are small, flexible and are believed to be capable of being maneuverable enough to reach the desired location within a patient's body.

One embodiment of the device 10 also includes a vacuum lumen 38. The vacuum lumen 38 is configured to be in fluid communication with a vacuum source and one or more vacuum ports 42 in the exterior of the elongated shaft 12. The vacuum ports 42 are in fluid communication with the vacuum lumen 38 to provide a vacuum within a body cavity.

In one embodiment the device 10 includes a cavity filling member 44 which at least in part fills the body cavity located on the distal portion 16 of the elongated shaft 12. The cavity filling member 44 can be inflatable or expandable and configured to contact tissue surfaces defining the body cavity. The cavity filling member 44 is in fluid communication with a first inflation lumen 46 which has a first inflation port 48. The vacuum ports 42 for the vacuum lumen 38 preferably are located proximal and or distal to the cavity filling member 44 which at least partially fills the body cavity.

Figure 3A:
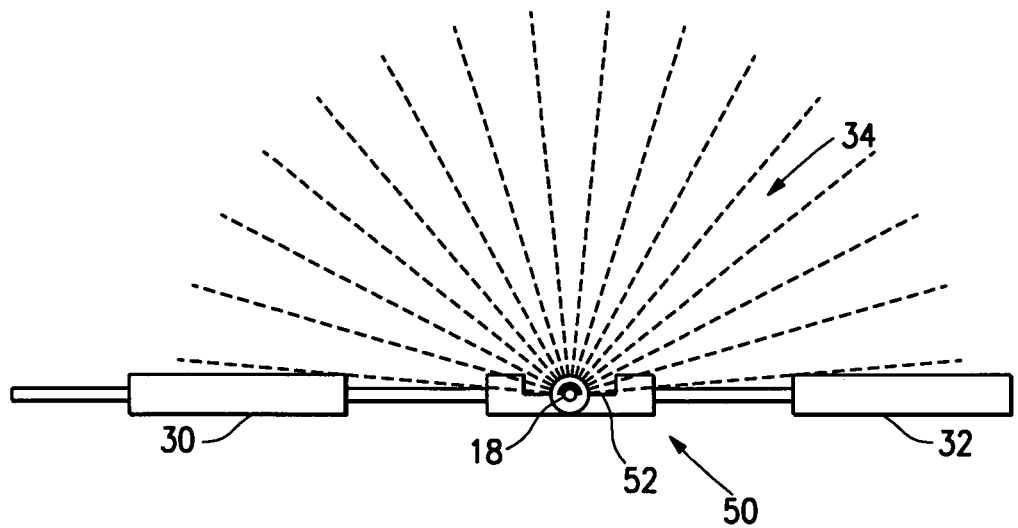
FIG. 3A is a diagramatic view of a central radiation shield disposed about a radiation source.
Figure 3B:
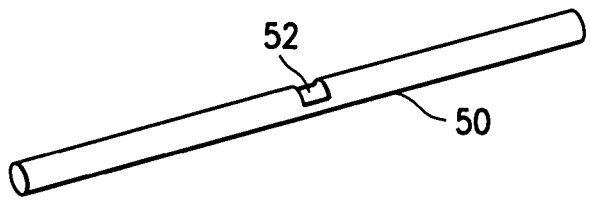
FIG. 3B is a perspective view and FIG. 3C is an elevational view of a central radiation shield including a window.
Figure 3D:
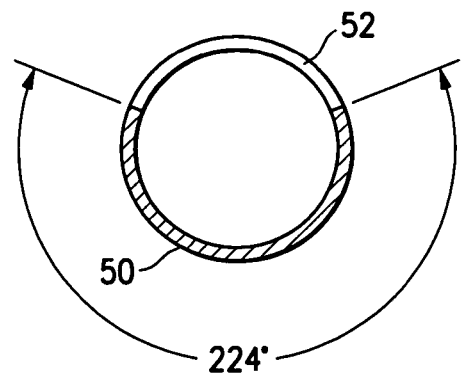
FIG. 3D is a transverse cross sectional view of the central radiation shield taken along lines 3D-3D in FIG. 3C.
Figure 3C:
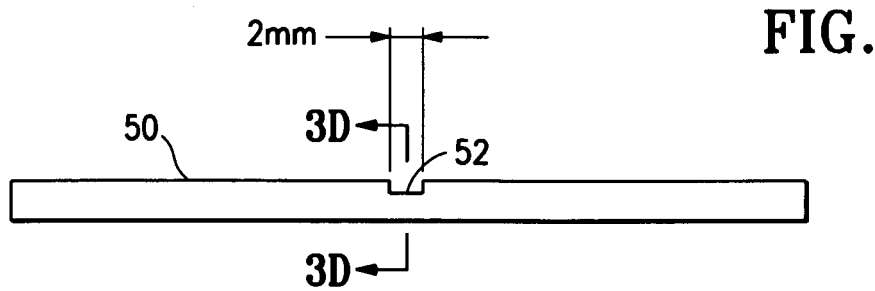
Figure 3E:
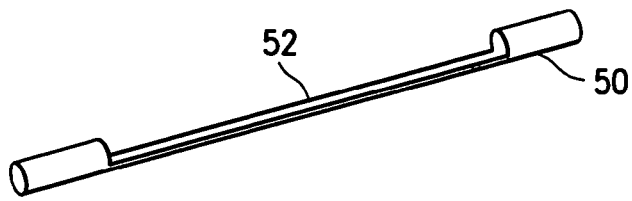
FIG. 3E is a perspective view and FIG. 3F is an elevational view of a central radiation shield including a window.
Figure 3G:
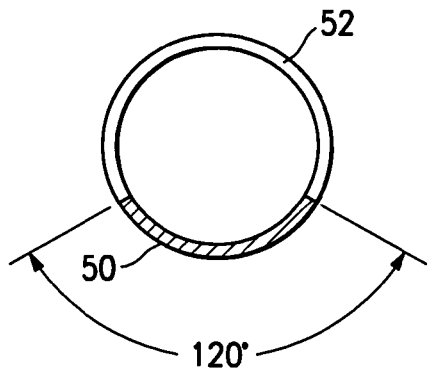
FIG. 3G is a transverse cross sectional view of the central radiation shield taken along lines 3G-3G in FIG. 3F.
Figure 3F:
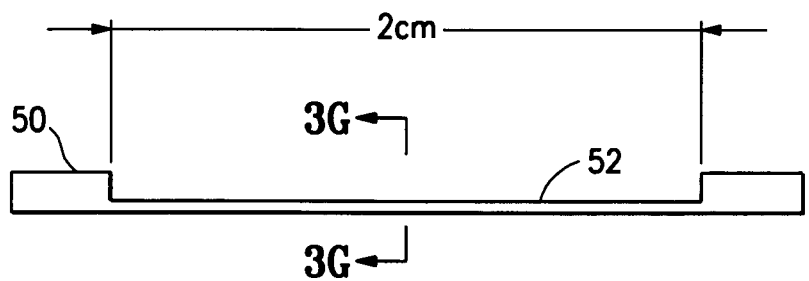

A central radiation shield 50, shown in FIG. 3A, can be deployed between the proximal 30 and distal 32 radiation shields. The central radiation shield 50 preferably defines at least in part a window 52 to allow for dispersal of radiation from a radiation source 18. Preferably the central radiation shield 50 defines a window 52 which may have a variable length as shown in FIGS. 3B-G. Preferably the length of the window 52 is between about 2 millimeters to 5 centimeters and the central radiation shield is tubular in shape. Preferably the shielded area is arcuate with an angular range from about 20° to about 240°. Alternatively the central radiation shield 50 comprises a pair of separately rotatable members to allow for adjusting the window dimensions. The central radiation shield 50 is rotated or advanced to position the window 52 near the target tissue.

Figure 4A:
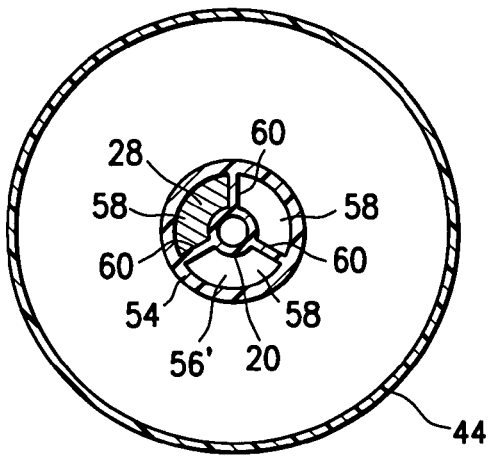
FIGS. 4A and 4B are transverse cross sectional views of an embodiment of the invention including three chambers, some of which contain radiation shields.
Figure 4B:
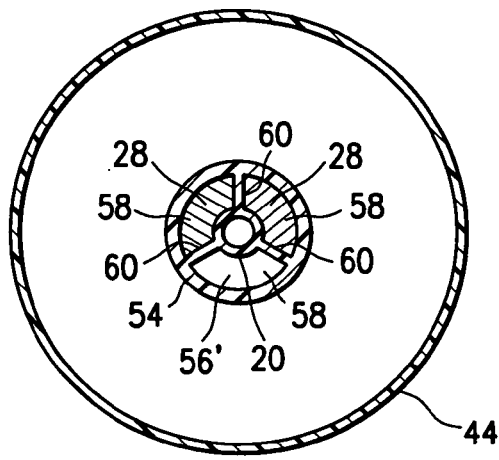

Another embodiment of the invention shown in FIGS. 4A and 4B includes a partitioned shaft 54 disposed about the delivery shaft 20. The partitioned shaft 54 has a lumen 56 which is divided into at least two chambers 58 by spacing elements 60. Radiation shields 28 are configured to be inserted into one or more chambers 58 through the proximal end of the elongate shaft 12 to surround at least a portion of the treatment location 14. The radiation shields 28 reduce or minimize irradiation of healthy portions of the body cavity while treating nearby areas with the radiation source 18.

In one possible embodiment the radiation shield 28 has varying densities acting as a filter to allow for some controlled amount of radiation to pass through yielding a non-symmetric radiation dosing. In another embodiment the radiation shields 28 are constructed of sintered metal to block radiation and still allow for a fluid pathway for suction or vacuum of the body cavity.

Figure 5A:
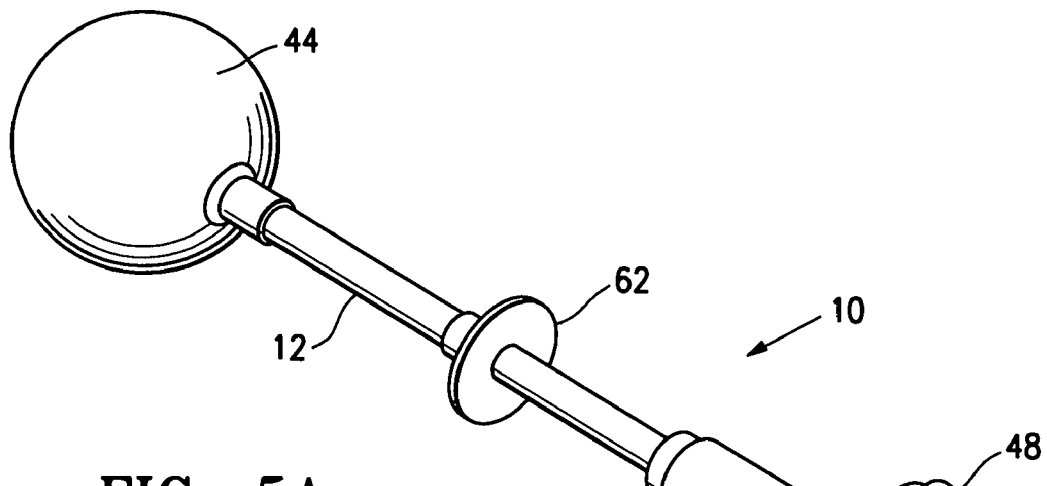
FIG. 5A is perspective view of a device embodying features of the invention including a sealing member which is formed of an adhesive material.
Figure 5B:
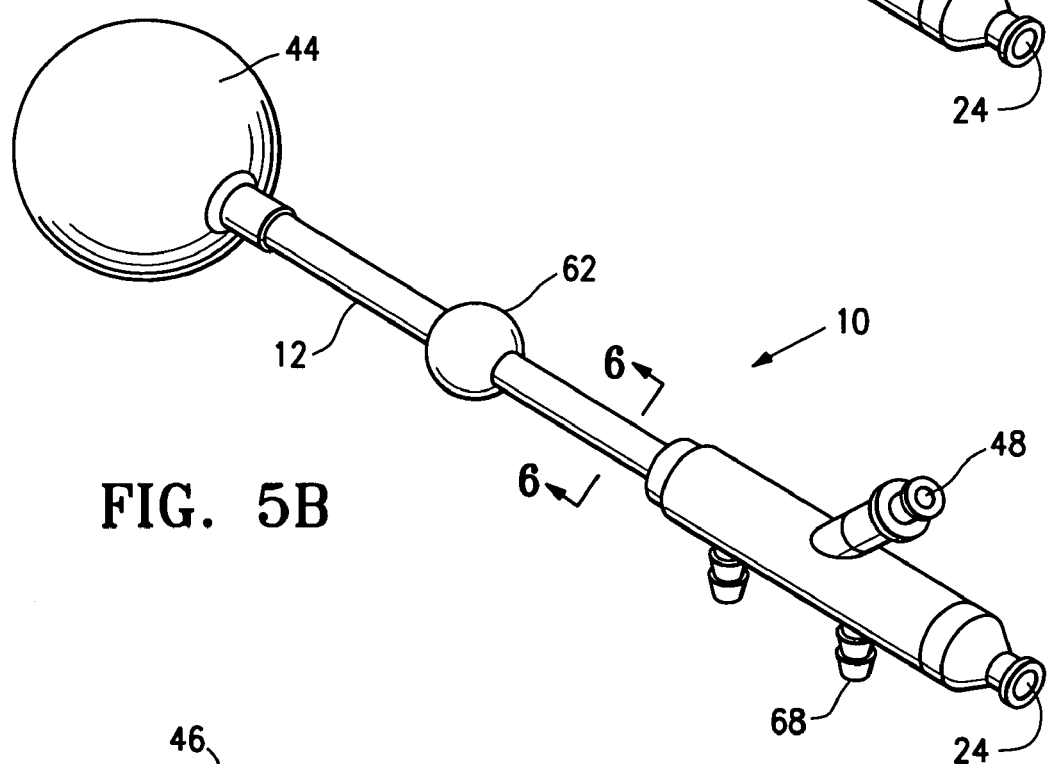
FIG. 5B is a perspective view of a device embodying features of the invention including an sealing member which is inflatable.
Figure 6:
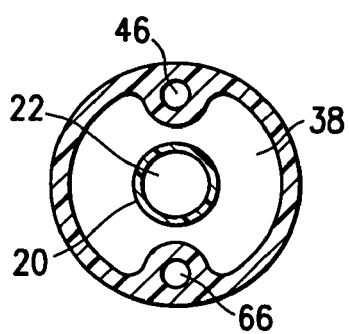
FIG. 6 is a cross sectional view of the device taken along line 6-6 in FIG. 5B.

In another embodiment of the invention depicted in FIGS. 5A, 5B and 6 the device includes an elongate shaft 12 with a sealing member 62 located on the elongate shaft 12 to seal the passageway 64 through which the device 10 is advanced. The sealing member can be inflated via a second inflation lumen 66 (FIGS. 5B and 6A) which is in fluid communication with a second inflation port 68 on the proximal end of the elongate shaft 12. The sealing member 62 allows for closer contact with the walls of the passageway 64. Preferably, the device 10 also includes a cavity filling member 44 which at least in part fills the body cavity and which is inflatable or expandable. The sealing member 62 is located on the elongate shaft 12 proximal to the distal end of the elongate shaft.

Alternatively, as shown in FIG. 5A, the device 10 can include a sealing member 62 formed of a flange or cuff having an adhesive distal face and located toward the proximal end of the elongate shaft 12. The sealing member 62 preferably is configured to form a seal in the passageway 64 leading to the body cavity by adhering to a patient's skin.

The device 10 preferably includes a vacuum lumen 38 configured to be in fluid communication with a proximal vacuum source and one or more vacuum ports 42 preferably proximal and or distal to the cavity filling member 44. Application of a vacuum within the vacuum lumen 38 aspirates fluid in the cavity through one or more vacuum ports 42 and pulls tissue defining the cavity onto the exterior of the cavity filling member 44 deployed within the cavity. As shown in FIG. 5B the sealing member 62 preferably is expanded or expandable, such as a balloon, and configured to minimize the loss of vacuum within the body cavity when a vacuum is developed.

A device 10 having features of the invention can include contoured pads for use on the elongate shaft 12 of the device 10. The contoured pads are provided on the proximal portion of the elongated shaft 12 of the device 10 and are configured to cover a portion of the shaft. The contoured pads preferably are comprised of material having soft tapered edges to minimize irritation to the skin caused by movement or dressing and undressing. The pads are taped externally to the patient or alternatively are attached to the patient with a double sided tape or adhesive material.

A device 10 having features of the invention can be provided, at least in part, with a lubricious coating, such as a hydrophilic material. The lubricious coating preferably is applied to the elongate shaft 12 or to the cavity filling member 44, if one is present, to reduce sticking and friction during insertion of a device 10. Hydrophilic coatings such as those provided by AST, Surmodics, TUA Systems, Hydromer, or STS Biopolymers are suitable.

A device 10 having features of the invention may also include an antimicrobial coating that covers all or a portion of the device 10 to minimize the risk of introducing of an infection during extended treatments. The antimicrobial coating preferably is comprised of silver ions impregnated into a hydrophilic carrier. Alternatively the silver ions are implanted onto the surface of the device 10 by ion beam deposition. The antimicrobial coating preferably is be comprised of an antiseptic or disinfectant such as chlorhexadiene, benzyl chloride or other suitable biocompatible antimicrobial materials impregnated into hydrophilic coatings. Antimicrobial coatings such as those provided by Spire, AST, Algon, Surfacine, Ion Fusion, or Bacterin International would be suitable. Alternatively a cuff member covered with the antimicrobial coating is provided on the elongated shaft of the delivery device 10 at the point where the device 10 enters the skin.

Figure 7A:
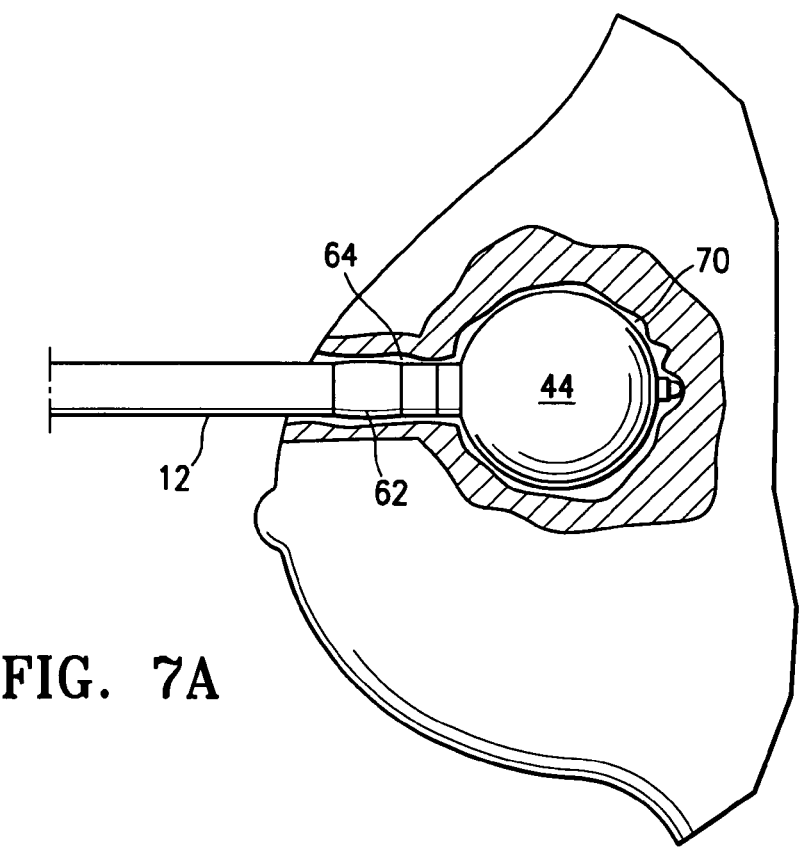
FIG. 7A and 7B show the steps of a preferred method for treating a body cavity.
Figure 7B:
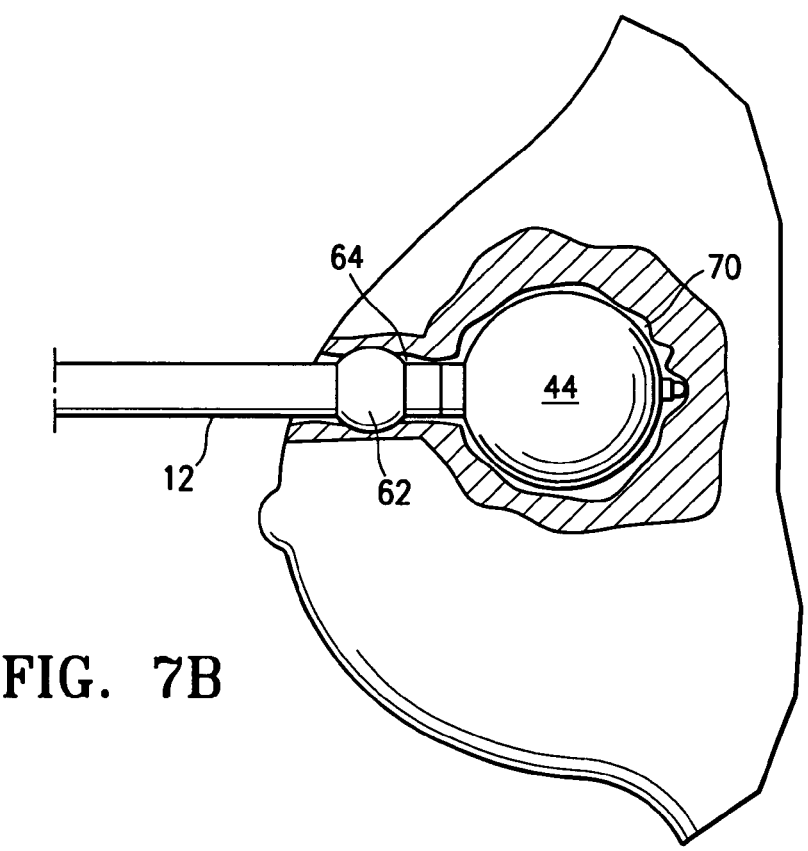

Methods for treating a body cavity 70 of a patient, shown in FIGS. 7A and 7B, include delivering a radiation source 18 to a body cavity 70 to treat the desired tissue adjacent a device 10 embodying features of the invention while minimizing damaging irradiation of healthy tissue. For example, a method of treating tissue adjacent a body cavity 70 includes inserting a device 10 embodying features of the invention into the body cavity 70, positioning a radiation shielding component 26 to shield healthy tissue in the body cavity 70 and positioning a source for a treatment agent, such as radiation source 18 within the treatment location 14 in a distal portion 16 of the shaft 12.

Methods for treating tissue adjacent a body cavity 70 include methods for sealing a passageway 64 leading to a body cavity 70. For example, a method of treating tissue adjacent a body cavity 70 includes inserting a device 10 embodying features of the invention into the body cavity 70 and sealing the passageway 64 leading to the body cavity 70 (FIG. 7A) and then at least in part contacting the passageway 64 with a sealing member 62 on the elongate shaft 12 (FIG. 7B).

While particular forms of the invention have been illustrated and described herein, it will be apparent that various modifications and improvements can be made to the invention. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention be defined by the scope of the appended claims as broadly as the prior art will permit.

Terms such as "element", "member", "component", "device", "means", "portion", "section", "steps" and words of similar import when used herein shall not be construed as invoking the provisions of 35 U.S.C §112(6) unless the following claims expressly use the terms "means" or "step" followed by a particular function without reference to a specific structure or action. All patents and all patent applications referred to above are hereby incorporated by reference in their entirety.

What is claimed is:

1. A device for irradiating a cavity within a patient from which tissue has been removed to treat tissue which surrounds the cavity, comprising:
   a.) an elongate shaft having a proximal end, a distal end, a treatment location at a distal portion of the shaft, the distal portion of the shaft being configured to be deployed within the body cavity;
   b.) a radiation source configured to be disposed in the treatment location and to irradiate tissue surrounding the body cavity; and
   c.) a radiation shielding component having a first shielding portion which has proximal and distal ends and which is configured to partially shield the radiation source when deployed within the treatment location in order absorb part of the radiation emitted from the radiation source to thereby protect a portion of the tissue surrounding the cavity shielded by the first radiation shielding portion and to allow irradiation treatment of tissue surrounding the cavity which is not shielded by the shielding component and a second tubular radiation shielding portion at one end of the shielding component; and
   d.) a cavity filling member surrounding the treatment location so as to space the radiation source within the cavity.

2. The device of claim 1 wherein the elongated shaft has a first lumen extending to the treatment location and the radiation shielding component is slidably disposed within the first lumen.

3. The device of claim 1 wherein the second radiation shielding portion is at the proximal end of the radiation component.

4. The device of claim 3 wherein a third radiation shielding portion is at the distal end of the radiation component.

5. The device of claim 1 wherein the radiation source is a solid material.

6. The device of claim 5 wherein the radiation source is a brachytherapy seed.

7. The device of claim 1 wherein the radiation source is selected from the group consisting of a liquid containing a radioactive iodine isotope, a slurry of solid isotope, a gel containing a radioactive isotope solid, or a microminiature x-ray tube.

8. The device of claim 2 wherein the radiation shielding component is slidably disposed within the first lumen of the elongate shaft.

9. The device of claim 3 wherein the first second and third radiation shield portions of the radiation shield component define at least in part a window configured to allow emission of radiation from the radiation source to a selected tissue region surrounding the cavity.

10. The device of claim 9 wherein the length of the window is about 2 millimeters to about 5 centimeters.

11. The device of claim 10 wherein the first radiation shield portion has an arcuate radiation shielding area with an angular range between about 20° to about 240°.

12. The device of claim 4 wherein spacing between the first and second radiation shield portions is adjustable.

13. The device of claim 2 wherein the elongated shaft has a second lumen configured to receive the radiation source and to facilitate advancement of the radiation source to the treatment location.

14. The device of claim 13 wherein the first lumen receiving the radiation shielding component is an annular lumen disposed about the second lumen in the shaft.

15. The device of claim 14 wherein the first annular lumen is divided into two or more chambers by spacing.

16. The device of claim 15 wherein the two or more chambers of the annular first lumen are configured to receive one or more radiation shields.

17. The device of claim 13 wherein the elongated shaft has a third lumen and the cavity filling member has an interior chamber which is in fluid communication with the third lumen through a first inflation port.

18. The device of claim 1 wherein the cavity filling member is expandable.

19. The device of claim 17 wherein the cavity filling member is inflatable.

20. The device of claim 19 wherein the cavity filling member has an interior configured to receive inflation fluid from the third lumen.

21. The device of claim 20 wherein the cavity filling member is a balloon.

22. The device of claim 1 wherein the cavity filling member is spherical shaped.

23. The device of claim 1 wherein the cavity filling member is oval shaped.

24. The device of claim 1 wherein the radiation shielding component is formed at least in part of radiation absorbing material.

25. The device of claim 24 wherein the radiation absorbing material is selected from a group consisting of tantalum, bismuth subcarbonate, barium sulfate, platinum, gold, and tungsten.

26. The device of claim 1 wherein a portion of the radiation shielding component contains a lesser amount of the radiation absorbing material than other portions of the radiation shielding component.

27. The device of claim 1 wherein the elongate shaft has a vacuum lumen configured to be in fluid communication with a vacuum source and one or more vacuum ports in an exterior of the elongate shaft are in fluid communication with the vacuum lumen to provide a vacuum within the body cavity.

28. A device for irradiating a cavity within a patient from which tissue has been removed to treat tissue which surrounds the cavity, comprising:
 a.) an elongate shaft having a proximal end, a distal end, and a treatment location in a distal portion of the elongate shaft;
 b.) a source for a radiation agent configured to be disposed in the treatment location to irradiate the cavity; and
 c.) a sealing member on the elongated shaft proximal to the treatment location which is configured to seal the shaft within a passageway leading to a body cavity.

29. The device of claim 28 wherein the radiation source is a brachytherapy seed.

30. The device of claim 28 wherein the radiation source is selected from the group consisting of a liquid containing a radioactive iodine isotope, a slurry of solid isotope, a gel containing a radioactive isotope solid, or a microminiature x-ray tube.

31. The device of claim 28 wherein the device has an inner lumen configured to deliver the treatment agent to the distal portion of the shaft.

32. The device of claim 31 wherein the device has a cavity filling member secured to the distal portion of the elongate shaft and configured to at least partially fill the body cavity.

33. The device of claim 32 wherein the device has a vacuum lumen configured to be in fluid communication with a vacuum source and with one or more vacuum ports in an exterior of the elongated shaft in fluid communication with the vacuum lumen to provide a vacuum within the body cavity.

34. The device of claim 28 wherein the sealing member is configured to expand within the passageway.

35. The device of claim 28 wherein the sealing member is configured to inflate within the passageway.

36. The device of claim 35 wherein the sealing member has an interior configured to receive inflation fluid.

37. The device of claim 28 wherein the sealing member is a balloon.

38. The device of claim 33 wherein the at least one vacuum port in fluid communication with the vacuum lumen is distal to the cavity filling member.

39. The device of claim 33 wherein the at least one vacuum port in fluid communication with the vacuum lumen is proximal to the cavity filling member.

40. The device of claim 32 wherein the cavity filling member is expandable.

41. The device of claim 32 wherein the cavity filling member is inflatable.

42. The device of claim 41 wherein the cavity filling member has an interior configured to receive inflation fluid.

43. The device of claim 32 wherein the cavity filling member is a balloon.

44. The device of claim 32 wherein the cavity filling member has a spherical shape.

45. The device of claim 32 wherein the cavity filling member is oval shaped.

* * * * *